(12) United States Patent
Koulechov et al.

(10) Patent No.: US 8,360,059 B2
(45) Date of Patent: Jan. 29, 2013

(54) RESPIRATOR WITH A BREATHING TUBE SYSTEM

(75) Inventors: Kirill Koulechov, Timm. Strand (DE); Ludger Tappehorn, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 776 days.

(21) Appl. No.: 12/543,146

(22) Filed: Aug. 18, 2009

(65) Prior Publication Data
US 2010/0043793 A1    Feb. 25, 2010

(30) Foreign Application Priority Data

Aug. 21, 2008  (DE) .......................... 10 2008 039 137

(51) Int. Cl.
*A61M 16/00* (2006.01)
*A62B 7/00* (2006.01)
*F24J 3/00* (2006.01)
*H05B 3/00* (2006.01)

(52) U.S. Cl. .............................. 128/204.17; 128/203.27
(58) Field of Classification Search ............ 128/200.24, 128/201.13, 202.21, 203.16–203.17, 203.26–203.27, 128/204.13, 204.17
See application file for complete search history.

(56) References Cited

U.S. PATENT DOCUMENTS

| | | | | |
|---|---|---|---|---|
| 5,357,948 A * | 10/1994 | Eilentropp | ............... | 128/204.17 |
| 5,454,061 A * | 9/1995 | Carlson | .................. | 392/478 |
| 5,537,996 A * | 7/1996 | McPhee | .................. | 128/204.17 |
| 5,701,887 A | 12/1997 | Rustad et al. | | |
| 5,988,164 A | 11/1999 | Paluch | | |
| 6,078,730 A * | 6/2000 | Huddart et al. | ............... | 392/480 |
| 6,167,883 B1 * | 1/2001 | Beran et al. | ............. | 128/203.17 |
| 6,953,354 B2 * | 10/2005 | Edirisuriya et al. | ......... | 439/191 |
| 7,588,029 B2 * | 9/2009 | Smith et al. | ............. | 128/203.17 |
| 8,078,040 B2 * | 12/2011 | Forrester | .................. | 392/481 |
| 2004/0250815 A1 * | 12/2004 | Scott et al. | .............. | 128/204.17 |
| 2006/0283447 A1 | 12/2006 | Dhuper et al. | | |
| 2008/0105257 A1 | 5/2008 | Klasek et al. | | |

FOREIGN PATENT DOCUMENTS

| | | |
|---|---|---|
| AU | 778842 | 12/2004 |
| DE | 102007003454 | 7/2008 |
| EP | 0 201 985 A1 | 11/1986 |
| EP | 0 672 430 A2 | 9/1995 |
| EP | 1 352 670 A1 | 10/2003 |
| EP | 1 743 672 A1 | 1/2007 |
| GB | 933172 | 8/1963 |
| WO | WO 2006/127257 | 11/2006 |

* cited by examiner

*Primary Examiner* — Oren Ginsberg
(74) *Attorney, Agent, or Firm* — McGlew and Tuttle, P.C.

(57) ABSTRACT

A breathing tube system for connection to a respirator (2), which is provided with a tube heater, avoids a local increase in temperature during the heating of the tube (4, 7). Resistance wires (9, 10) are connected to one another on the breathing tubes (4, 7) in the form of a series connection and are contacted at the respirator (2) in the area of an inspiration port (3) and of an expiration port (6).

14 Claims, 6 Drawing Sheets

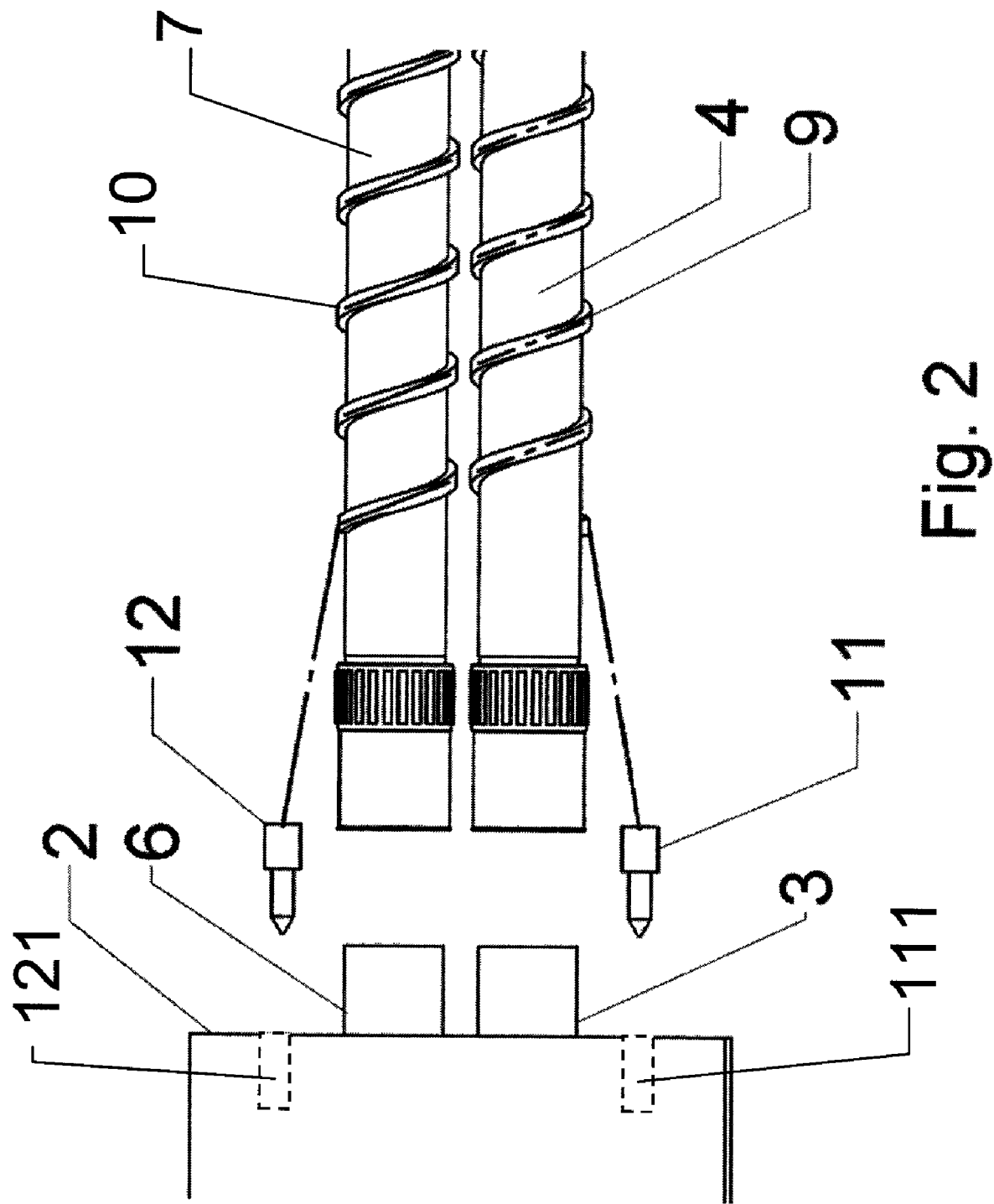

RESPIRATOR WITH A BREATHING TUBE SYSTEM

CROSS REFERENCE TO RELATED APPLICATIONS

This application claims the benefit of priority under 35 U.S.C. §119 of German Patent Application DE 10 2008 039 137.9 filed Aug. 21, 2008, the entire contents of which are incorporated herein by reference.

FIELD OF THE INVENTION

The present invention pertains to a combination of a respirator and a breathing tube system and a respirator for connection to a breathing tube system.

BACKGROUND OF THE INVENTION

Patients who are artificially respirated in an intensive care unit receive breathing air, which is adapted to the physiological needs of the patient in terms of temperature and humidity. Active humidifiers, which heat and humidify the breathing gas, are used for this. A water-filled container, through which the gas to be inspired is sent and is enriched with moisture, is located within the humidifier. The breathing tubes are usually provided with a tube heater to prevent condensation of moisture within the breathing tube system.

A breathing tube with resistance wires arranged helically on the outside is known, for example, from U.S. Pat. No. 5,357,948. One or two resistance wires are provided, which extend helically on the outside of the breathing tube. Furthermore, a separate, non-heatable conductor for the return line is located on the outside. The resistance wires may be connected either in series or in parallel, the resistance wires being contacted electrically via a tube end.

The drawback of the prior-art breathing tube is that short-circuit may develop within the forward line and the return line in case of damage to the insulation of the resistance wires, which is possibly associated locally with intense heating of the tube. The tube may become damaged hereby, and leaks, through which breathing gas can escape, may also develop at such a site.

SUMMARY OF THE INVENTION

The basic object of the present invention is to improve a device with a respirator and a breathing tube system such that a local increase in temperature is avoided during the heating of the tube.

According to the invention, a combination respirator and breathing tube system is provided. The combination comprises a respirator with an inspiration port for releasing gas to be inspired and an expiration port for receiving expired gas. The breathing tube system comprises an inspiration tube at the inspiration port and an expiration tube at the expiration port. Each of the inspiration tube and the expiration tube is provided with a tube heater including resistance wires connected to one another in the form of a series connection and having an electrical connector contact at the inspiration port and an electrical connector contact at the expiration port.

According to another aspect of the invention, a respirator is provided comprising a respirator device with an inspiration port and an expiration port, an inspiration tube connected to the inspiration port and an expiration tube connected to the expiration port. A tube heater is provided in contact with the expiration tube and with the inspiration tube. The tube heater includes resistance wires connected to one another in series and a first plug-type electric connection with a plug part connected to the resistance wires and connected to a plug receptacle at or adjacent to the inspiration port and a second plug-type electric connection with a plug part connected to the resistance wires and connected to a plug receptacle at or adjacent to the expiration port.

The resistance wires may advantageously extend spirally on the inspiration tube and extend spirally on the expiration tube. The resistance wires may advantageously be present in different winding densities in the areas of at least one of the inspiration tube and the expiration tube.

The breathing tube system may be provided in the form of an endless tube, provided with a heating coil with a predetermined breaking point in the area of the patient port.

Provisions are made according to the present invention for the resistance wire to extend on the breathing tube as a single-wire line from the inspiration tube to the expiration tube and to be electrically contacted in the area of the inspiration port and the expiration port. For the electrical contacting, the connection sockets of the inspiration tube and of the expiration tube are especially preferably designed such that the electrical connection with the resistance wires can also be established besides the gas connection. The breathing tubes are usually connected to one another via a Y-piece, and the breathing gas is fed to the patient via the Y-piece. The resistance wires especially preferably extend helically on the inspiration tube or on the expiration tube. To generate different heating outputs in the area of the inspiration tube or the expiration tube, the resistance wires may be present with different winding densities on the inspiration tube or on the expiration tube. It is especially preferable to heat the expiration tube more intensely than the inspiration tube, because the expired gas has a saturated breathing gas moisture content and intensified condensation may occur there.

The breathing tube used especially preferably is an extruded endless tube, which is provided with a predetermined breaking point in such a way that the tube can be divided into an inspiration tube and an expiration tube without the resistance wires being interrupted in the area of the Y-piece. The use of an extruded endless tube also has the advantage that breathing tubes can be cut and adapted to the patient's needs individually.

Exemplary embodiments of the present invention are shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a side view of an electrical connection between breathing tubes and a respirator;

DESCRIPTION OF THE PREFERRED EMBODIMENTS

Figure 1:
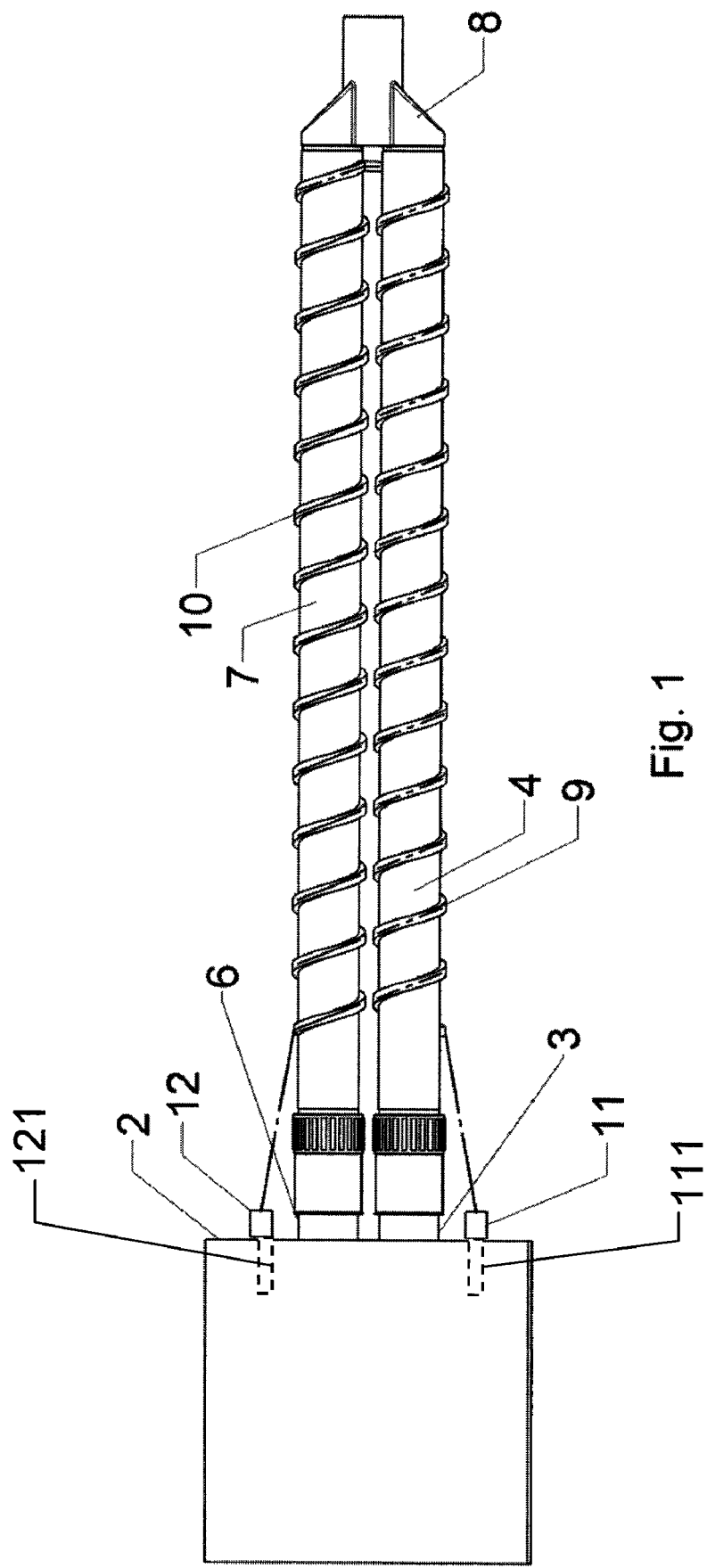
FIG. 1 is a respirator with a breathing tube system according to a first embodiment of the invention.

Referring to the drawings in particular, FIG. 1 schematically shows a respiration system 1, comprising a respirator 2 with an inspiration port 3, an inspiration tube 4, an expiration port 6, an expiration tube 7 and a Y-piece 8 between the inspiration tube 4 and the expiration tube 7. The inspiration tube 4 and the expiration tube 7 have a tube heater in the form of resistance wires 9, 10 fastened helically on the outside. The resistance wires 9, 10 are connected to one another in the form of a series connection and are contacted via single-pole electric plug-type connections 11, 111, 121, 12 at the inspiration port 3 and the expiration port 6. The current flows via a first plug-type part 11, resistance wire 9, resistance wire 10 and a second plug-type part 12. Inspiration tube 4 and expiration tube 7 are parts of an extended endless tube so that the resistance wires are not interrupted.

FIG. 2 illustrates as an example the mechanical and electrical contact at the inspiration tube 4 and at the expiration tube 4. Resistance wire 9 of the inspiration tube 4 is connected to a first plug part 11, inserted into a plug first receptacle 111 of the respirator 2. Resistance wire 10 of the expiration tube 7 is connected to a second plug part 12, inserted into a second plug receptacle 121 of the repirator.

Figure 3A:
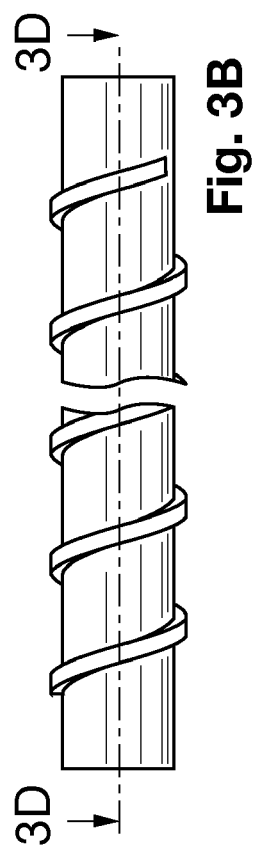
FIG. 3A is a side view of an inspiration tube.
Figure 3B:
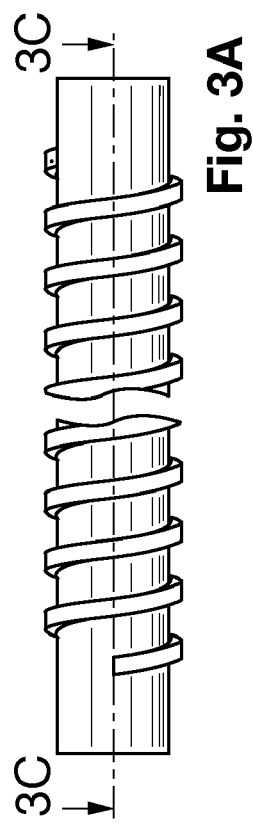
FIG. 3B is a side view of an expiration tube.
Figure 3C:
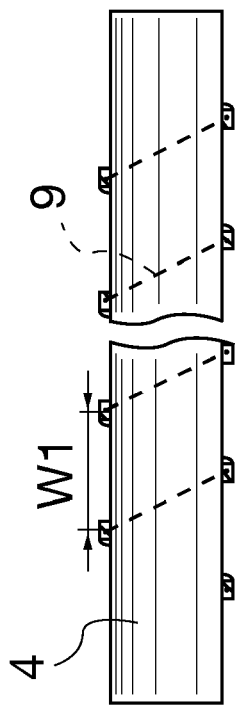
FIG. 3C is a sectional view of the inspiration tube with the section taken along line 3C-3C of FIG. 3A.
Figure 3D:
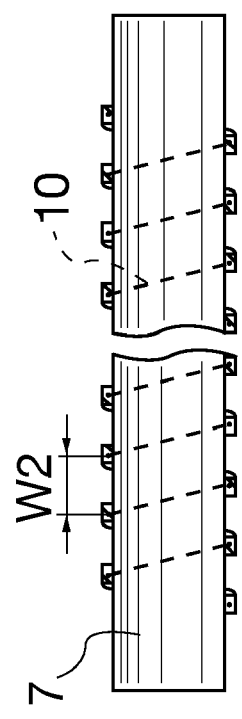
FIG. 3D is a sectional view of the inspiration tube with the section taken along line 3B-3B of FIG. 3B with FIGS. 3A and 3C showing a different winding density of the inspiration tube compared to a winding density of the expiration tube shown in FIGS. 3B and 3D.

FIGS. 3A-3D show advantageous embodiment variants of the inspiration tube 4 with the resistance wire 9 and of the expiration tube 7 with the resistance wire 10. To set different heating outputs in the inspiration tube 4 and in the expiration tube 7, the resistance wires 9, 10 have different winding densities, which are designated by W1 for the inspiration tube and by W2 for the expiration tube 7 in FIGS. 3C and 3D. To avoid condensation of moisture, the expiration tube 7 is heated more intensely than the inspiration tube 4. The expiration tube 7 contains more heating windings per unit of length than the inspiration tube 4, as a result of which the distance between two windings W1 on the inspiration tube 4 is greater than the distance W2 between the windings on the expiration tube 7. FIGS. 3A and 3B respectively show a side view of the inspiration tube 4 and of the expiration tube 7, while the corresponding sectional view is shown in FIGS. 3C and 3D.

Figure 4:
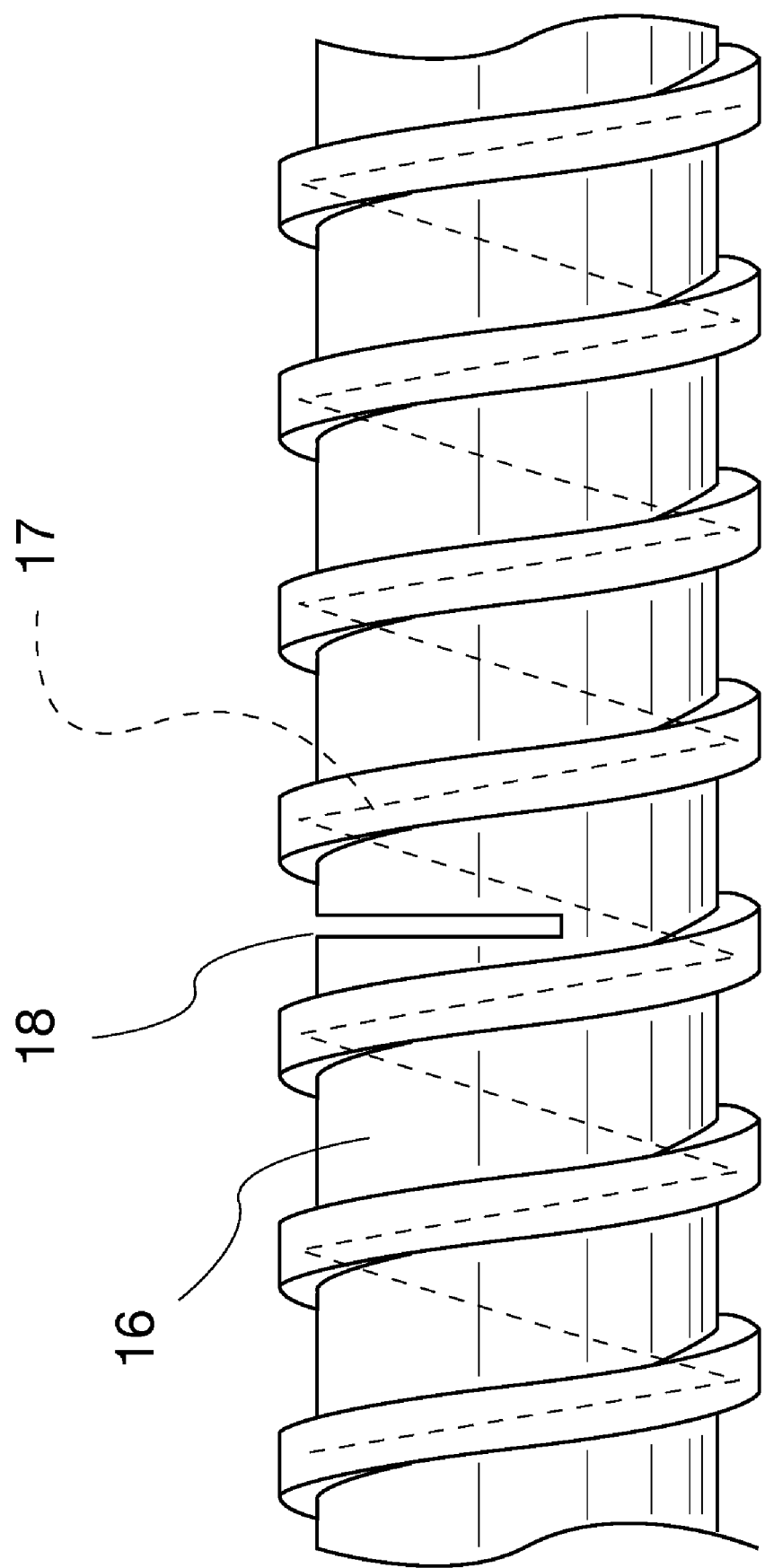
FIG. 4 is an endless tube with a predetermined breaking point.
Figure 5:
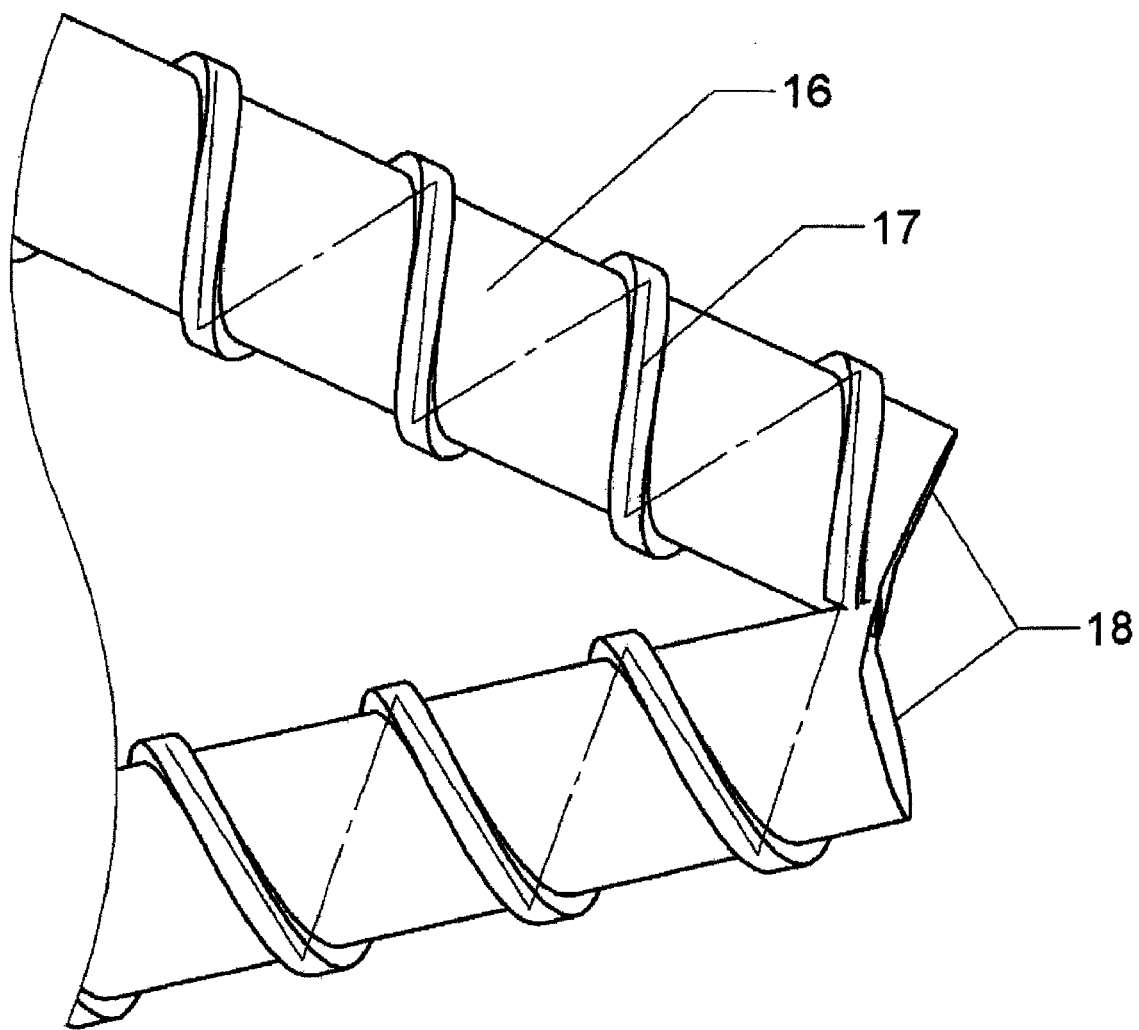
FIG. 5 is a tube cut out in the area of the predetermined breaking point corresponding to FIG. 4.

FIG. 4 shows an advantageous embodiment variant in the form of an endless tube 16 with a heating coil 17 and with a predetermined breaking point 18. The predetermined breaking point 18 is designed such that, as is schematically shown in FIG. 5, the heating coil 17 is not damaged when tube 16 is cut up.

Figure 6B:
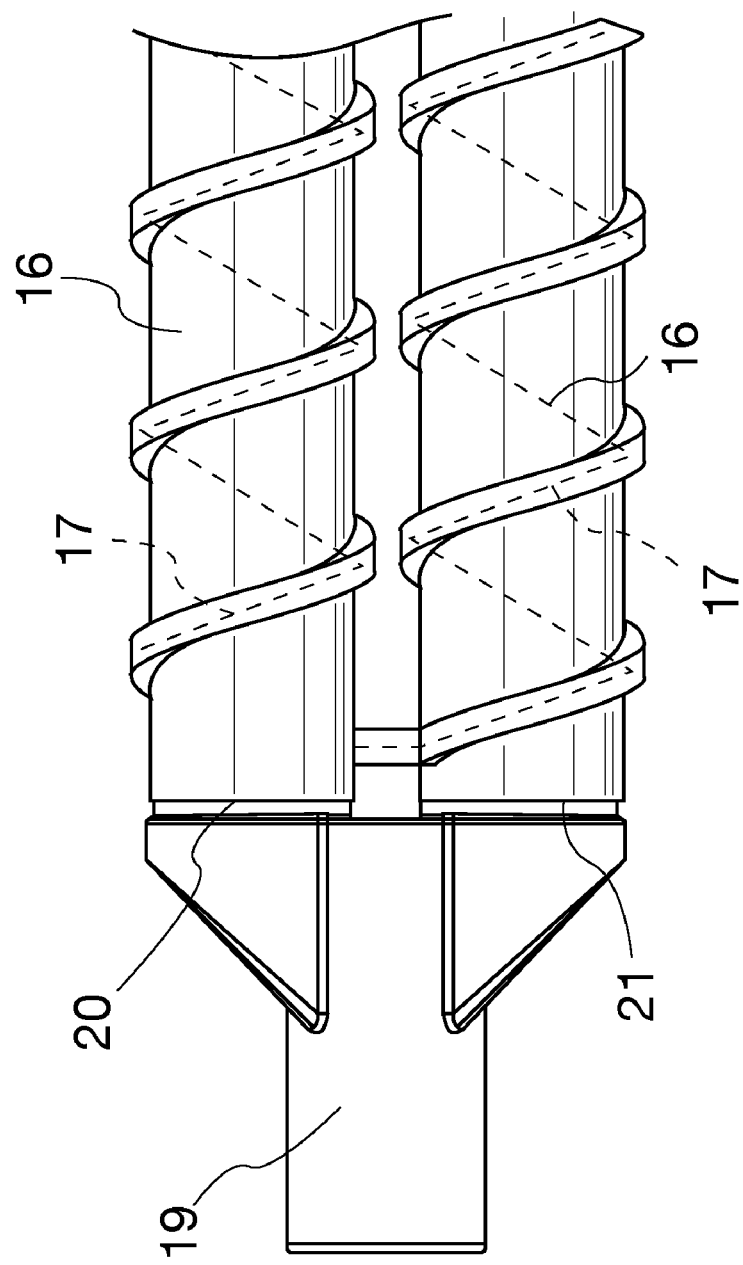
FIG. 6B is the endless tube according to FIG. 5 with the Y-piece.
Figure 6A:
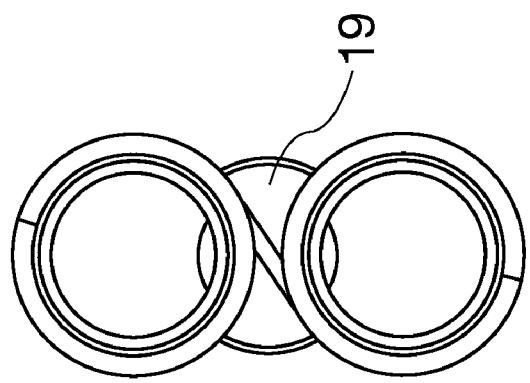
FIG. 6A is an end view of the tube according to FIG. 5 showing a Y-piece.

FIGS. 6A and 6B show the endless tube 16 in the area of the predetermined breaking point 18 combined with a Y-piece 19. By bending off the heating coil 17 in the area of the predetermined breaking point 18, the Y-piece 19 can be inserted directly into the tube ends 20, 21 without electrical contacting of the heating coil 17 having to be performed. An end view of the endless tube 16 is shown in FIG. 6A.

While specific embodiments of the invention have been shown and described in detail to illustrate the application of the principles of the invention, it will be understood that the invention may be embodied otherwise without departing from such principles.

APPENDIX

List of Reference Numbers

1 Respiration system
2 Respirator
3 Inspiration port
4 Inspiration tube
6 Expiration port
7 Expiration tube
8 Y-piece
9, 10 Resistance wire
11 First plug part
12 Second plug part
16 Endless tube
17 Heating coil
18 Predetermined breaking point
19 Y-piece
20, 21 Tube end
111 First plug receptacle
121 Second plug receptacle

What is claimed is:

1. A combination of a respirator and a breathing tube system, the combination comprising:
    a respirator with an inspiration port for releasing gas to be inspired and an expiration port for receiving expired gas; and
    a breathing tube system comprising an inspiration tube at the inspiration port and an expiration tube at the expiration port, each of the inspiration tube and the expiration tube being provided with a tube heater including resistance wires connected to one another in the form of a series connection and having an electrical connector contact at the inspiration port and an electrical connector contact at the expiration port, wherein said breathing tube system is formed from a combined length tube with a single wire, said combined length tube comprising a predetermined breaking point in the area of a patient port.

2. A device in accordance with claim 1, wherein said resistance wires extend spirally on the inspiration tube and extend spirally on the expiration tube.

3. A device in accordance with claim 1, wherein said resistance wires are present in different winding densities in the areas of at least one of the inspiration tube and the expiration tube.

4. A device in accordance with claim 1, wherein said inspiration tube comprises an inspiration tube first end and an inspiration tube second end, said inspiration tube first end being connected to said inspiration port, said expiration tube having an expiration tube first end and an expiration tube second end, said expiration tube first end being connected to said expiration port, said inspiration tube second end and said expiration tube second end being connected to said patient port, said inspiration tube and said expiration tube defining a gap in an area adjacent to said patient port, at least a portion of said tube heater extending continuously, without interruption, from said inspiration tube to said expiration tube in said area adjacent to said patient port, whereby said at least said portion of said tube heater bridges said gap.

5. A respirator comprising:
a respirator device with an inspiration port and an expiration port;
an inspiration tube having an inspiration tube first end and an inspiration tube second end, said inspiration tube first end being connected to said inspiration port;
an expiration tube having an expiration tube first end and an expiration tube second end, said expiration tube first end being connected to said expiration port;
a patient port, said inspiration tube second end and said expiration tube second end being connected to said patient port, said inspiration tube and said expiration tube defining a gap in an area adjacent to said patient port; and
a tube heater in contact with said expiration tube and with said inspiration tube, said tube heater including resistance wires connected to one another in series and a first plug-type electric connection with a plug part connected to said resistance wires and connected to a plug receptacle at or adjacent to said inspiration port and a second plug-type electric connection with a plug part connected to said resistance wires and connected to a plug receptacle at or adjacent to said expiration port, at least a portion of said tube heater extending continuously, without interruption, from said inspiration tube to said expiration tube in said area adjacent to said patient port, whereby said at least said portion of said tube heater bridges said gap.

6. A respirator in accordance with claim 5, wherein said resistance wires extend spirally on the inspiration tube and extend spirally on the expiration tube.

7. A respirator in accordance with claim 5, wherein said resistance wires are present in different winding densities in the areas of at least one of the inspiration tube and the expiration tube.

8. A respirator in accordance with claim 5, wherein said inspiration tube and said expiration tube are formed from a tube having a single wire and a combined length greater than or equal to a length of said inspiration tube and said expiration tube.

9. A respirator comprising:
a respirator device with an inspiration port and an expiration port;
an inspiration tube connected to said inspiration port;
an expiration tube connected to said expiration port, said inspiration tube and said expiration tube being formed from a tube comprising a predetermined breaking point and said tube comprising a combined length equal to or greater than a length of said inspiration tube and said expiration tube; and
a tube heater in contact with said expiration tube and with said inspiration tube, said tube heater including a resistance wire extending on the inspiration tube and on the expiration tube as a continuous single-wire line from the inspiration tube to the expiration tube and an electrical connection contact connected to the single-wire line and connected to an electrical connection receptacle in the area at or adjacent to said inspiration port and connected to an electrical connection receptacle in the area at or adjacent to said expiration port.

10. A respirator according to claim 9, wherein the electrical connection contact comprises a first plug-type electric connection with a plug part connected to said single-wire line and connected to a plug receptacle at or adjacent to said inspiration port and a second plug-type electric connection with a plug part connected to said single-wire line and connected to a plug receptacle at or adjacent to said expiration port.

11. A respirator in accordance with claim 9, wherein said single-wire line extends spirally on the inspiration tube and extends spirally on the expiration tube.

12. A respirator in accordance with claim 9, wherein said single-wire line is present in different winding densities in the areas of at least one of the inspiration tube and the expiration tube.

13. A respirator in accordance with claim 9, wherein said single-wire line is not separated when said tube is separated at said predetermined breaking point to form said inspiration tube and said expiration tube.

14. A respirator in accordance with claim 9, further comprising:
a patient port, said inspiration tube having an inspiration tube first end and an inspiration tube second end, said inspiration tube first end being connected to said inspiration port, said expiration tube having an expiration tube first end and an expiration tube second end, said expiration tube first end being connected to said expiration port, said inspiration tube second end and said expiration tube second end being connected to said patient port, said inspiration tube and said expiration tube defining a gap in an area adjacent to said patient port, at least a portion of said tube heater extending continuously, without interruption, from said inspiration tube to said expiration tube in said area adjacent to said patient port, whereby said at least said portion of said tube heater bridges said gap.

* * * * *